United States Patent
Sugahara et al.

(10) Patent No.: US 10,961,285 B2
(45) Date of Patent: Mar. 30, 2021

(54) MOLDED ARTICLE AND METHOD FOR PRODUCING MOLDED ARTICLE

(71) Applicants: Spiber Inc., Yamagata (JP); Kojima Industries Corporation, Aichi (JP)

(72) Inventors: Junichi Sugahara, Yamagata (JP); Kaori Sekiyama, Yamagata (JP); Ayumi Abe, Yamagata (JP); Junichi Shimokata, Yamagata (JP); Junichi Noba, Aichi (JP); Shinji Hirai, Hokkaido (JP)

(73) Assignees: Spiber Inc., Yamagata (JP); Kojima Industries Corporation, Aichi (JP)

( * ) Notice: Subject to any disclaimer, the term of this patent is extended or adjusted under 35 U.S.C. 154(b) by 0 days.

(21) Appl. No.: 15/760,497

(22) PCT Filed: Sep. 8, 2016

(86) PCT No.: PCT/JP2016/076501
§ 371 (c)(1),
(2) Date: Mar. 15, 2018

(87) PCT Pub. No.: WO2017/047504
PCT Pub. Date: Mar. 23, 2017

(65) Prior Publication Data
US 2019/0040109 A1    Feb. 7, 2019

(30) Foreign Application Priority Data

Sep. 18, 2015 (JP) .............................. JP2015-185777

(51) Int. Cl.
*C07K 14/43*    (2006.01)
*B29C 43/02*    (2006.01)
(Continued)

(52) U.S. Cl.
CPC ...... *C07K 14/43518* (2013.01); *B29C 43/003* (2013.01); *B29C 43/02* (2013.01); *C08H 1/00* (2013.01); *B29K 2089/00* (2013.01)

(58) Field of Classification Search
None
See application file for complete search history.

(56) References Cited

U.S. PATENT DOCUMENTS 8,666,471 B2    3/2014  Rogers et al.
2009/0075868 A1  3/2009  Keeley et al.
(Continued)

FOREIGN PATENT DOCUMENTS

CN    102892356 A    1/2013
CN    103502516 A    1/2014
(Continued)

OTHER PUBLICATIONS

Xu & Lewis, "Structure of a protein superfiber: Spider dragline silk", Proc. Nati. Acad. Sci. USA, 1990, vol. 87, pp. 7120-7124.*
(Continued)

*Primary Examiner* — Suzanne M Noakes
(74) *Attorney, Agent, or Firm* — Morgan, Lewis & Bockius LLP

(57) ABSTRACT

Provided is a molded article of a composition comprising a polypeptide, wherein the polypeptide is at least one kind selected from the group consisting of natural spider silk protein and polypeptides derived from natural spider silk protein.

8 Claims, 3 Drawing Sheets

Specification includes a Sequence Listing.

(51) Int. Cl.
*C08H 1/00* (2006.01)
*B29C 43/00* (2006.01)
*C07K 14/435* (2006.01)

(56) References Cited

U.S. PATENT DOCUMENTS

| | | | |
|---|---|---|---|
| 2010/0228359 | A1 | 9/2010 | Vogt et al. |
| 2014/0058066 | A1 | 2/2014 | Sekiyama et al. |
| 2015/0291673 | A1* | 10/2015 | Sekiyama ........ C07K 14/43518 530/353 |

FOREIGN PATENT DOCUMENTS

| | | | |
|---|---|---|---|
| CN | 104718244 A | | 6/2015 |
| CN | 104936979 A | | 9/2015 |
| JP | H05-171049 A | | 7/1993 |
| JP | 2010-526582 A | | 8/2010 |
| JP | 2014-080491 A | | 5/2014 |
| JP | 2014-129639 A | | 7/2014 |
| JP | 2014-198715 A | | 10/2014 |
| WO | 2008/071226 A1 | | 6/2008 |
| WO | 2008/140703 A2 | | 11/2008 |
| WO | WO 2012/165476 | * | 12/2012 |
| WO | 2014/062134 A1 | | 4/2014 |
| WO | 2014/103799 A1 | | 7/2014 |
| WO | 2014/175179 A1 | | 10/2014 |
| WO | 2017/047503 A1 | | 3/2017 |

OTHER PUBLICATIONS

Tucker et al., "Mechanical and Physical Properties of Recombinant Spider Silk Films Using Organic and Aqueous Solvents", BioMacromolecules, Jul. 2014, vol. 15, pp. 3158-3170. dx.doi.org/10.1021/bm5007823.*

Hirai, "Keratin and Fibroin Resins for Environmental Friendly Materials Using Animal Proteins Derived from Industrial Wastes;" Functions & Materials, 34: 40-48 (2014) (partial English translation).

International Search Report issued in corresponding International Patent Application No. PCT/JP2016/076501 dated Oct. 11, 2016.

Supplemental European Search Report issued in counterpart European Patent Application No. 16846375.0 dated Jan. 8, 2019.

International Preliminary Report on Patentability and Written Opinion issued in corresponding International Patent Application No. PCT/JP2016/076501 dated Mar. 29, 2018.

Akiyama et al., "Effect of preparation method of powdered silk on the mechanical properties of moulded silk," Polymer, 35: 2355-2358 (1994).

Guerette et al., "Silk Properties Determined by Gland-Specific Expression of a Spider Fibroin Gene Family," Science, 272: 112-115 (1996).

"Pressing of Powder Silk and the Properties of the Molded Product," Modern Silk Science & Technology, 8-12 (1994) (see partial English translation).

* cited by examiner (a)

(b)

(c)

```
                        SEQUENCE LISTING

<160> NUMBER OF SEQ ID NOS: 12

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45

Leu Ala
    50

<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ser Ile Gly Gln Ile Asn
            20                  25                  30

<210> SEQ ID NO 3
<211> LENGTH: 21
```

```
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 24
<212> TYPE: PRT
<213> ORGANISM: Artificial Sequence
<220> FEATURE:
<223> OTHER INFORMATION: His tag and start codon

<400> SEQUENCE: 4

Met His His His His His His His His Ser Ser Gly Ser Ser
1               5                   10                  15

Leu Glu Val Leu Phe Gln Gly Pro
            20

<210> SEQ ID NO 5
<211> LENGTH: 660
<212> TYPE: PRT
<213> ORGANISM: Artificial Sequence
<220> FEATURE:
<223> OTHER INFORMATION: recombinant spider silk protein ADF3Kai

<400> SEQUENCE: 5

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gly Pro Gly Ser Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
                100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220
```

```
Ala Ala Ala Gly Gly Tyr Gly Pro Gly Ser Gly Gln Gln Gly Pro Gly
225                 230                 235                 240
Gln Gln Gly Pro Gly Gln Gln Gly Pro Gly Gln Gln Gly Pro Tyr Gly
                245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gln Gln Gly Pro
        275                 280                 285
Tyr Gly Pro Gly Ala Ser Ala Ala Ser Ala Ala Gly Gly Tyr Gly
        290                 295                 300
Pro Gly Ser Gly Gln Gln Gly Pro Gly Gln Gln Gly Pro Gly Gly Gln
305                 310                 315                 320
Gly Pro Tyr Gly Pro Gly Ala Ser Ala Ala Ala Ala Ala Gly Gly
                325                 330                 335
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gln Gly Pro Tyr Gly
                355                 360                 365
Pro Gly Ala Ser Ala Ala Ala Ala Ala Gly Gly Tyr Gly Pro Gly
370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Ala Gly Ala Ala Gly
                435                 440                 445
Gly Tyr Gly Pro Gly Ser Gly Gln Gln Gly Pro Gly Gln Gln Gly Pro
        450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
        515                 520                 525
Gly Gly Gln Gly Pro Tyr Gly Pro Gly Ala Ala Ser Ala Ala Val Ser
        530                 535                 540
Val Gly Gly Tyr Gly Pro Gln Ser Ser Val Pro Val Ala Ser Ala
545                 550                 555                 560
Val Ala Ser Arg Leu Ser Ser Pro Ala Ala Ser Ser Arg Val Ser Ser
                565                 570                 575
Ala Val Ser Ser Leu Val Ser Ser Gly Pro Thr Lys His Ala Ala Leu
                580                 585                 590
Ser Asn Thr Ile Ser Ser Val Val Ser Gln Val Ser Ala Ser Asn Pro
                595                 600                 605
Gly Leu Ser Gly Cys Asp Val Leu Val Gln Ala Leu Leu Glu Val Val
                610                 615                 620
Ser Ala Leu Val Ser Ile Leu Gly Ser Ser Ile Gly Gln Ile Asn
625                 630                 635                 640
Tyr Gly Ala Ser Ala Gln Tyr Thr Gln Met Val Gly Gln Ser Val Ala
```

```
            645               650               655
Gln Ala Leu Ala
        660
```

<210> SEQ ID NO 6
<211> LENGTH: 1983
<212> TYPE: DNA
<213> ORGANISM: Artificial Sequence
<220> FEATURE:
<223> OTHER INFORMATION: recombinant DNA of spider silk protein gene
      ADF3Kai

<400> SEQUENCE: 6

```
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggccctt cgcaacaagg tcccgggcag     240
caaggtcctg gtggccaggg tccctacggg ccggggcga gtgcgcagc agccgctgca       300
ggcggttatg gtccaggaag cggacagcaa ggtccgggag gtcaaggtcc gtatggccca     360
ggctctagcg cggctgccgc tgccgcgggt ggcaacggac agggagcgg acaacagggc      420
gcgggacaac agggtccagg acagcaaggc caggggcgt cggcggctgc agcggcggcc      480
ggaggctatg acccggctc aggacaacag ggaccgggtc aacaaggacc cggtggccaa      540
ggccctatg gcccgggcgc cagcgcggcc gcagccgccg cgggcgggta cggccccggt      600
agcggccagg gaccaggtca gcaggggcca ggaggtcagg gcccatacgg tccgggcgca     660
tccgcggcgg cggcagcggc aggtggctac ggtcccggaa gcggccaaca ggggccaggg     720
caacaaggac caggacaaca aggtcctggg ggccaaggac gtatggacc aggagcatca      780
gctgcagccg cggcagctgg cggttacggt ccaggctacg gccagcaggg tccgggtcag     840
cagggaccgg gaggccaggg gccttatggc cctggcgctt ccgcagccag tgccgcttct     900
ggaggatacg gccgggaag cggtcagcaa ggccctggcc aacaaggacc tggaggccaa      960
gggccctacg gccaggagc ctcggcagcc gcagctgccg caggtgggta tgggccaggt     1020
agcgggcaac aagggccggg tcagcaagga ccggggcaac agggacctgg cagcaagga    1080
cccgggggtc aaggcccgta cggacctggt gcgtctgcag ctgctgctgc ggctggtgga    1140
tatggtccgg gatcggggca gcagggtccc ggtcagcagg gcctggtca gcaagggcca     1200
ggccaacagg gacccggaca acaaggcccg gtcaacagg gtcctggaca gcagggccg     1260
ggccaacaag gccctgggca acaggtccg ggggacagg gggcctatgg gcctggcgca      1320
tctgccgccg ctggcgcagc cggtgggtac gggcctggt caggtcaaca ggggcctggt     1380
caacaaggcc ccgggcaaca gggcccggc cagcaaggtc cagggcagca gggcccggga     1440
cagcaagggc ctggacaaca ggggcccgga cagcaggga cttacgggcc cggtgcgagc     1500
gcagcggccg ccgccgcagg gggatatgc cccggatcgg ccagcaggg accaggccag     1560
caaggacctg gccaacaggg cccgggggt caggggccgt atggtcccgg cgctgcaagt    1620
gctgcagtgt ccgttggagg ttacggccct cagtcttcgt ctgttccggt ggcgtccgca    1680
gttgcgagta gactgtcttc acctgctgct tcatcgcgag tatcgagcgc tgtttcgtct   1740
cttgtctcgt cgggtcccac gaaacatgcc gccctttcaa atacgatttc atctgtagtg   1800
tcccaagtta gtgcaagtaa cccggggtta tccggatgcg acgttctcgt tcaggcactc   1860
ctagaagtag tatccgcgtt ggtgagcatc ttaggcagct cctcgatagg tcaaataaac   1920
```

```
tatggtgctt cagcccagta tacacagatg gtgggacaga gcgtcgcgca ggcattggct    1980
taa                                                                 1983
```

<210> SEQ ID NO 7
<211> LENGTH: 542
<212> TYPE: PRT
<213> ORGANISM: Artificial Sequence
<220> FEATURE:
<223> OTHER INFORMATION: recombinant DNA of spider silk protein gene
      ADF3Kai

<400> SEQUENCE: 7

```
Met His His His His His His His His His Ser Ser Gly Ser Ser
1               5                   10                  15

Leu Glu Val Leu Phe Gln Gly Pro Ala Arg Ala Gly Ser Gly Gln Gln
                20                  25                  30

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gln Gly Pro Tyr Gly Pro Gly Ala Ser Ala Ala
            85                  90                  95

Ala Ala Ala Ala Gly Gly Tyr Gly Pro Gly Ser Gly Gln Gln Gly Pro
                100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
            245                 250                 255

Pro Gly Ala Ser Ala Ala Ala Ala Ala Ala Gly Gly Tyr Gly Pro Gly
                260                 265                 270

Tyr Gly Gln Gln Gly Pro Gly Gln Gln Gly Pro Gly Gln Gly Pro
        275                 280                 285

Tyr Gly Pro Gly Ala Ser Ala Ala Ser Ala Ala Ser Gly Gly Tyr Gly
    290                 295                 300

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Ala Gly Gly
                325                 330                 335
```

-continued

```
Tyr Gly Pro Gly Ser Gly Gln Gln Gly Pro Gly Gln Gln Gly Pro Gly
                340                 345                 350
Gln Gln Gly Pro Gly Gln Gln Gly Pro Gly Gln Gln Gly Pro Tyr Gly
            355                 360                 365
Pro Gly Ala Ser Ala Ala Ala Ala Ala Gly Gly Tyr Gly Pro Gly
        370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Ala Gly Ala Ala Gly
        435                 440                 445
Gly Tyr Gly Pro Gly Ser Gly Gln Gln Gly Pro Gly Gln Gln Gly Pro
    450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
        500                 505                 510
Ser Gly Gln Gln Gly Pro Gly Gln Gln Gly Pro Gly Gln Gln Gly Pro
    515                 520                 525
Gly Gly Gln Gly Pro Tyr Gly Pro Gly Ala Ala Ser Ala Ala
    530                 535                 540

<210> SEQ ID NO 8
<211> LENGTH: 434
<212> TYPE: PRT
<213> ORGANISM: Artificial
<220> FEATURE:
<223> OTHER INFORMATION: Recombinang spider silk protein ADF4Kai

<400> SEQUENCE: 8

Met His His His His His His His His His Ser Ser Gly Ser Ser
1               5                   10                  15
Leu Glu Val Leu Phe Gln Gly Pro Ala Gly Ser Ser Ala Ala Ala
            20                  25                  30
Ala Ala Ala Ser Gly Ser Gly Gly Tyr Gly Pro Glu Asn Gln Gly Pro
        35                  40                  45
Ser Gly Pro Val Ala Tyr Gly Pro Gly Gly Pro Val Ser Ser Ala Ala
    50                  55                  60
Ala Ala Ala Ala Ala Gly Ser Gly Pro Gly Gly Tyr Gly Pro Glu Asn
65                  70                  75                  80
Gln Gly Pro Ser Gly Pro Gly Gly Tyr Gly Pro Gly Gly Ser Gly Ser
                85                  90                  95
Ser Ala Ala Ala Ala Ala Ala Ala Ser Gly Pro Gly Gly Tyr Gly
            100                 105                 110
Pro Gly Ser Gln Gly Pro Ser Gly Pro Gly Gly Ser Gly Gly Tyr Gly
        115                 120                 125
Pro Gly Ser Gln Gly Ala Ser Gly Pro Gly Gly Pro Gly Ala Ser Ala
    130                 135                 140
Ala Ala Ala Ala Ala Ala Ala Ala Ser Gly Pro Gly Gly Tyr Gly
145                 150                 155                 160
```

```
Pro Gly Ser Gln Gly Pro Ser Gly Pro Gly Ala Tyr Gly Pro Gly Gly
            165                 170                 175

Pro Gly Ser Ser Ala Ala Ala Ala Ala Ala Ala Ser Gly Pro Gly
        180                 185                 190

Gly Tyr Gly Pro Gly Ser Gln Gly Pro Ser Gly Pro Gly Val Tyr Gly
            195                 200                 205

Pro Gly Gly Pro Gly Ser Ser Ala Ala Ala Ala Ala Ala Ala Gly Ser
            210                 215                 220

Gly Pro Gly Gly Tyr Gly Pro Glu Asn Gln Gly Pro Ser Gly Pro Gly
225                 230                 235                 240

Gly Tyr Gly Pro Gly Gly Ser Gly Ser Ser Ala Ala Ala Ala Ala Ala
            245                 250                 255

Ala Ala Ser Gly Pro Gly Gly Tyr Gly Pro Gly Ser Gln Gly Pro Ser
            260                 265                 270

Gly Pro Gly Gly Ser Gly Gly Tyr Gly Pro Gly Ser Gln Gly Gly Ser
            275                 280                 285

Gly Pro Gly Ala Ser Ala Ala Ala Ala Ala Ala Ala Ser Gly Pro
            290                 295                 300

Gly Gly Tyr Gly Pro Gly Ser Gln Gly Pro Ser Gly Pro Gly Tyr Gln
305                 310                 315                 320

Gly Pro Ser Gly Pro Gly Ala Tyr Gly Pro Ser Pro Ser Ala Ser Ala
            325                 330                 335

Ser Val Ala Ala Ser Val Tyr Leu Arg Leu Gln Pro Arg Leu Glu Val
            340                 345                 350

Ser Ser Ala Val Ser Ser Leu Val Ser Ser Gly Pro Thr Asn Gly Ala
            355                 360                 365

Ala Val Ser Gly Ala Leu Asn Ser Leu Val Ser Gln Ile Ser Ala Ser
            370                 375                 380

Asn Pro Gly Leu Ser Gly Cys Asp Ala Leu Val Gln Ala Leu Leu Glu
385                 390                 395                 400

Leu Val Ser Ala Leu Val Ala Ile Leu Ser Ser Ala Ser Ile Gly Gln
            405                 410                 415

Val Asn Val Ser Ser Val Ser Gln Ser Thr Gln Met Ile Ser Gln Ala
            420                 425                 430

Leu Ser

<210> SEQ ID NO 9
<211> LENGTH: 355
<212> TYPE: PRT
<213> ORGANISM: Artificial
<220> FEATURE:
<223> OTHER INFORMATION: Recombinant spider silk protein MaSp2_N

<400> SEQUENCE: 9

Met His His His His His His Ser Ser Gly Ser Ser Leu Glu Val Leu
1               5                   10                  15

Phe Gln Gly Pro Ala Arg Ala Gly Pro Gly Gly Tyr Arg Pro Gly Gln
            20                  25                  30

Gln Gly Pro Ser Gly Pro Gly Ser Ala Ala Ala Ala Ala Ala Ala
        35                  40                  45

Ala Gly Pro Gly Gly Tyr Gly Pro Gly Gln Gln Gly Pro Gly Gly Tyr
            50                  55                  60

Gly Pro Gly Gln Gln Gly Pro Ser Gly Ala Gly Ser Ala Ala Ala Ala
65                  70                  75                  80

Ala Ala Ala Gly Pro Gly Gln Gln Gly Leu Gly Gly Tyr Gly Pro Gly
```

```
                    85                  90                  95
Gln Gln Gly Pro Gly Gly Tyr Gly Pro Gly Gln Gln Gly Pro Gly Gly
                    100                 105                 110

Tyr Gly Pro Gly Ser Ala Ser Ala Ala Ala Ala Ala Gly Pro Gly
            115                 120                 125

Gln Gln Gly Pro Gly Gly Tyr Gly Pro Gly Gln Gln Gly Pro Ser Gly
        130                 135                 140

Pro Gly Ser Ala Ser Ala Ala Ala Ala Ala Gly Pro Gly Gly Tyr
145                 150                 155                 160

Gly Pro Gly Gln Gln Gly Pro Gly Gly Tyr Ala Pro Gly Gln Gln Gly
                165                 170                 175

Pro Ser Gly Pro Gly Ser Ala Ala Ala Ala Ala Ala Arg Ala
            180                 185                 190

Gly Pro Gly Gly Tyr Gly Pro Ala Gln Gln Gly Pro Ser Gly Pro Gly
                195                 200                 205

Ile Ala Ala Ser Ala Ala Ser Ala Gly Pro Gly Gly Tyr Gly Pro Ala
        210                 215                 220

Gln Gln Gly Pro Ala Gly Tyr Gly Pro Gly Ser Ala Val Ala Ala Ser
225                 230                 235                 240

Ala Gly Ala Gly Ser Ala Gly Tyr Gly Pro Gly Ser Gln Ala Ser Ala
                245                 250                 255

Ala Ala Ser Arg Leu Ala Ser Pro Asp Ser Gly Ala Arg Val Ala Ser
            260                 265                 270

Ala Val Ser Asn Leu Val Ser Ser Gly Pro Thr Ser Ala Ala Leu
        275                 280                 285

Ser Ser Val Ile Ser Asn Ala Val Ser Gln Ile Gly Ala Ser Asn Pro
        290                 295                 300

Gly Leu Ser Gly Cys Asp Val Leu Ile Gln Ala Leu Leu Glu Ile Val
305                 310                 315                 320

Ser Ala Cys Val Thr Ile Leu Ser Ser Ser Ile Gly Gln Val Asn
            325                 330                 335

Tyr Gly Ala Ala Ser Gln Phe Ala Gln Val Val Gly Gln Ser Val Leu
        340                 345                 350

Ser Ala Phe
        355

<210> SEQ ID NO 10
<211> LENGTH: 559
<212> TYPE: PRT
<213> ORGANISM: Artificial
<220> FEATURE:
<223> OTHER INFORMATION: Recombinant spider silk protein Flag_92_short2

<400> SEQUENCE: 10

Met His His His His His His His His Ser Ser Gly Ser Ser
1               5                   10                  15

Leu Glu Val Leu Phe Gln Gly Pro Gly Ala Gly Gly Ser Gly Pro Gly
                20                  25                  30

Gly Ala Gly Pro Gly Gly Val Gly Pro Gly Gly Ser Gly Pro Gly Gly
            35                  40                  45

Val Gly Pro Gly Gly Ser Gly Pro Gly Gly Val Gly Pro Gly Gly Ser
        50                  55                  60

Gly Pro Gly Gly Val Gly Pro Gly Gly Ala Gly Pro Tyr Gly Pro
65                  70                  75                  80

Gly Gly Ser Gly Pro Gly Gly Ala Gly Gly Ala Gly Gly Pro Gly Gly
```

-continued

```
                85                  90                  95
Ala Tyr Gly Pro Gly Gly Ser Tyr Gly Pro Gly Gly Ser Gly Gly Pro
                    100                 105                 110
Gly Gly Ala Gly Gly Pro Tyr Gly Pro Gly Gly Glu Gly Pro Gly Gly
                    115                 120                 125
Ala Gly Gly Pro Tyr Gly Pro Gly Gly Ala Gly Gly Pro Tyr Gly Pro
            130                 135                 140
Gly Gly Ala Gly Gly Pro Tyr Gly Pro Gly Gly Glu Gly Gly Pro Tyr
145                 150                 155                 160
Gly Pro Gly Gly Ser Tyr Gly Pro Gly Gly Ala Gly Gly Pro Tyr Gly
                165                 170                 175
Pro Gly Gly Pro Tyr Gly Pro Gly Gly Glu Gly Pro Gly Gly Ala Gly
                    180                 185                 190
Gly Pro Tyr Gly Pro Gly Gly Val Gly Pro Gly Gly Gly Pro Gly Gly
                195                 200                 205
Gly Tyr Gly Pro Gly Gly Ala Gly Pro Gly Gly Tyr Gly Pro Gly Gly
            210                 215                 220
Ser Gly Pro Gly Gly Tyr Gly Pro Gly Gly Ser Gly Pro Gly Gly Tyr
225                 230                 235                 240
Gly Pro Gly Gly Ser Gly Pro Gly Gly Tyr Gly Pro Gly Gly Ser Gly
                245                 250                 255
Pro Gly Gly Tyr Gly Pro Gly Gly Ser Gly Pro Gly Gly Ser Gly Pro
                    260                 265                 270
Gly Gly Tyr Gly Pro Gly Gly Ser Gly Pro Gly Gly Ser Gly Pro Gly
                275                 280                 285
Gly Tyr Gly Pro Gly Gly Ser Gly Pro Gly Gly Tyr Gly Pro Gly Gly
            290                 295                 300
Ser Gly Pro Gly Gly Ser Gly Pro Gly Gly Tyr Gly Pro Gly Gly Ser
305                 310                 315                 320
Gly Pro Gly Gly Ser Gly Pro Gly Gly Tyr Gly Pro Gly Gly Ser Gly
                325                 330                 335
Pro Gly Gly Phe Gly Pro Gly Gly Phe Gly Pro Gly Gly Ser Gly Pro
                    340                 345                 350
Gly Gly Tyr Gly Pro Gly Gly Ser Gly Pro Gly Gly Ala Gly Pro Gly
                355                 360                 365
Gly Val Gly Pro Gly Gly Phe Gly Pro Gly Gly Ala Gly Pro Gly Gly
            370                 375                 380
Ala Gly Pro Gly Gly Ala Gly Pro Gly Gly Ala Gly Pro Gly Gly Ala
385                 390                 395                 400
Gly Pro Gly Gly Ala Gly Pro Gly Gly Ala Gly Pro Gly Gly Ala Gly
                405                 410                 415
Pro Gly Gly Ala Gly Gly Ala Gly Gly Ala Gly Gly Ala Gly Gly Ser
                    420                 425                 430
Gly Gly Ala Gly Gly Ser Gly Gly Thr Thr Ile Ile Glu Asp Leu Asp
                435                 440                 445
Ile Thr Ile Asp Gly Ala Asp Gly Pro Ile Thr Ile Ser Glu Glu Leu
            450                 455                 460
Thr Ile Ser Ala Tyr Tyr Pro Ser Ser Arg Val Pro Asp Met Val Asn
465                 470                 475                 480
Gly Ile Met Ser Ala Met Gln Gly Ser Gly Phe Asn Tyr Gln Met Phe
                485                 490                 495
Gly Asn Met Leu Ser Gln Tyr Ser Ser Gly Ser Gly Thr Cys Asn Pro
                    500                 505                 510
```

Asn Asn Val Asn Val Leu Met Asp Ala Leu Leu Ala Ala Leu His Cys
        515                 520                 525

Leu Ser Asn His Gly Ser Ser Ser Phe Ala Pro Ser Pro Thr Pro Ala
        530                 535                 540

Ala Met Ser Ala Tyr Ser Asn Ser Val Gly Arg Met Phe Ala Tyr
545                 550                 555

<210> SEQ ID NO 11
<211> LENGTH: 1629
<212> TYPE: DNA
<213> ORGANISM: Artificial Sequence
<220> FEATURE:
<223> OTHER INFORMATION: recombinant spider silk protein gene
      ADF3Kai-noNR

<400> SEQUENCE: 11

| | | |
|---|---|---|
| atgcatcacc atcatcatca tcaccaccac cattcctcgg gctcatcctt ggaagtgtta | 60 |
| tttcaaggac cagcacgagc cggttcggga caacaagggc ctggccagca gggcccaggt | 120 |
| caacaagggc caggacagca gggtccttat gggcccggcg caagcgcagc agctgcggcc | 180 |
| gctggtggct atggtcctgg ctccggtcaa cagggcccct cgcaacaagg tcccgggcag | 240 |
| caaggtcctg gtgccaggg tccctacggg ccggggcga gtgcggcagc agccgctgca | 300 |
| ggcggttatg gtccaggaag cggacagcaa ggtccgggag gtcaaggtcc gtatggccca | 360 |
| ggctctagcg cggctgccgc tgccgcgggt ggcaacggac agggagcgg acaacagggc | 420 |
| gcgggacaac agggtccagg acagcaaggc ccaggggcgt cggcggctgc agcggcggcc | 480 |
| ggaggctatg acccggctc aggacaacag ggaccgggtc aacaaggacc cggtggccaa | 540 |
| ggcccctatg cccgggcgc cagcgcggcc gcagccgccg cggcggta cggcccggt | 600 |
| agcggccagg accaggtca gcaggggcca ggaggtcagg gcccatacgg tccgggcgca | 660 |
| tccgcggcgg cggcagcggc aggtggctac ggtcccggaa gcggccaaca ggggccaggg | 720 |
| caacaaggac caggacaaca aggtcctggg ggccaaggac cgtatggacc aggagcatca | 780 |
| gctgcagccg cggcagctgg cggttacggt ccaggctacg ccagcaggg tccgggtcag | 840 |
| cagggaccgg gaggccaggg gccttatggc cctggcgctt ccgcagccag tgccgcttct | 900 |
| ggaggatacg ggccgggaag cggtcagcaa ggccctggcc aacaaggacc tggaggccaa | 960 |
| gggccctacg gccaggagc ctcggcagcc gcagctgccg caggtgggta tgggccaggt | 1020 |
| agcgggcaac aagggccggg tcagcaagga ccggggcaac agggacctgg cagcaagga | 1080 |
| cccgggggtc aaggcccgta cggacctggt gcgtctgcag ctgctgctgc ggctggtgga | 1140 |
| tatggtccgg atcggggca gcagggtccc ggtcagcagg gcctggtca gcaagggcca | 1200 |
| ggccaacagg gacccggaca acaaggcccg gtcaacagg gtcctggaca gcaggggccg | 1260 |
| ggccaacaag gcctgggca acagggtccg ggggacagg gggcctatgg gcctggcgca | 1320 |
| tctgccgccg ctggcgcagc cggtgggtac gggcctgggt caggtcaaca ggggcctggt | 1380 |
| caacaaggcc ccgggcaaca gggccccggc agcaaggtc agggcagca gggcccggga | 1440 |
| cagcaagggc ctggacaaca ggggcccgga cagcaggac cttacgggcc cggtgcgagc | 1500 |
| gcagcggccg ccgccgcagg gggatatggc cccggatcgg gccagcaggg accaggccag | 1560 |
| caaggacctg gccaacaggg cccgggggt caggggccgt atggtcccgg cgctgcaagt | 1620 |
| gctgcataa | 1629 |

<210> SEQ ID NO 12

```
<211> LENGTH: 5
<212> TYPE: PRT
<213> ORGANISM: Artificial Sequence
<220> FEATURE:
<223> OTHER INFORMATION: synthetic
<220> FEATURE:
<221> NAME/KEY: MISC_FEATURE
<222> LOCATION: (5)..(5)
<223> OTHER INFORMATION: Xaa is one amino acid selected from the group
      consisting of Ala, Ser, Tyr, and Val.

<400> SEQUENCE: 12

Gly Pro Gly Gly Xaa
1               5
```

MOLDED ARTICLE AND METHOD FOR PRODUCING MOLDED ARTICLE

SEQUENCE LISTING SUBMISSION VIA EFS-WEB

A computer readable text file, entitled "SequenceListing.txt" created on or about Jul. 22, 2019 with a file size of about 35 kb contains the sequence listing for this application and is hereby incorporated by reference in its entirety.

TECHNICAL FIELD

The present invention relates to a molded article and a method for producing a molded article.

BACKGROUND ART

For the purpose of weight reduction, cost reduction, the facilitation of forming, and the like, attempts for substituting metallic materials with organic materials are underway. As the above-described organic materials, phenolic resins having a high resin hardness are often used, and a method of adding a phenolic resin fiber to a matrix resin containing a phenolic resin is known since the bending elastic modulus or the bending strength is further increased (for example, refer to Patent Literature 1). In addition, due to a rising demand for environmental protection, bioplastics which are petroleum free materials have been thus far drawing attention, and the fact that formed articles having 4.5 GPa of a bending elastic modulus can be obtained by resinifying silk powder is known (for example, refer to Non Patent Literature 1).

CITATION LIST

Patent Literature

[Patent Literature 1] JP 2014-80491 A

Non Patent Literature

[Non Patent Literature 1] Shinji HIRAI, Monthly Journal of Function & Materials, June 2014, "Keratin and Fibroin Resins For Environmental Friendly Materials Using Animal Proteins Derived from Industrial Wastes"

SUMMARY OF INVENTION

Technical Problem

However, materials as disclosed by Patent Literature 1 are materials that are caused to exhibit a reinforcement effect by adding a fiber thereto, and it is difficult to obtain a high strength with the matrix resin alone. In addition, it is not possible to obtain formed articles having a bending elastic modulus of more than 4.5 GPa from biodegradable materials.

Therefore, an object of the present invention is to provide a biodegradable formed article that exhibits an excellent bending elastic modulus without using any additive materials such as reinforced fibers and a production method therefore.

Solution to Problem

The present invention provides a molded article of a composition comprising a polypeptide, wherein the polypeptide is at least one kind selected from natural spider silk protein and polypeptides derived from natural spider silk protein.

The above-described formed article has characteristics of being biodegradable, including natural spider silk protein and/or a polypeptide derived from natural spider silk protein as a raw material, and additionally, being obtained by molding the raw material and, due to these characteristics, exhibits an extremely high bending elastic modulus (for example, more than 4.5 GPa) even without using any additive materials such as reinforced fibers. Furthermore, the formed article can also be imparted with transparency and thus, compared with resins having a high strength but lacking transparency such as phenolic resins or polyether ether ketone (PEEK), the formed article has an advantage of significantly broadening applicable uses. Additionally, spider silk protein can be genetically modified in diverse manners, and thus it is possible to easily optimize the performance depending on the final uses. Meanwhile, the bending elastic modulus is preferably 4.7 GPa or more, more preferably 5.0 GPa or more, and still more preferably 5.2 GPa or more. The upper limit of the bending elastic modulus is not limited, but can be set to, for example, 15.0 GPa or less. The bending elastic modulus can be set to 10.0 GPa or less and, furthermore, 7.0 GPa or less.

The molded article may be provided as a hot press-molded article. The molded article refers to an article or the like formed using a casting mold (mold), but articles having a superior bending elastic modulus can be produced by hot pressing procedure.

The molded article can be produced using a production method comprising a step of hot pressing a composition comprising at least one kind selected from the group consisting of natural spider silk protein and polypeptides derived from natural spider silk protein.

Advantageous Effects of Invention

According to the present invention, a biodegradable formed article exhibiting an excellent bending elastic modulus without using any additive materials such as reinforced fibers and a production method therefore are provided.

DESCRIPTION OF EMBODIMENTS

Figure 1:
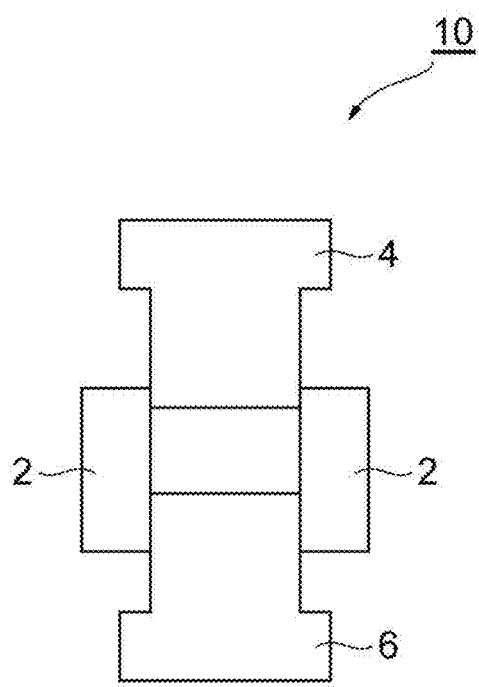
FIG. 1 is a schematic cross-sectional view of a press molding machine.

Hereinafter, a preferred embodiment of the present invention will be described. However, the present invention is not limited to the following embodiment by any means.

A molded article according to the embodiment is made of a composition comprising natural spider silk protein and/or a polypeptide derived from natural spider silk protein. The molded article can be obtained by introducing the above-described composition into a casting mold (mold) and carrying out forming or the like and, in the forming step, heating and/or pressing is possible. The composition has, typically, a shape of a powder form (lyophilized powder or the like) or a fibrous shape (a fiber or the like obtained by spinning), and the molded article may be a fused article of a composition including natural spider silk protein and/or a polypeptide derived from natural spider silk protein which have the above-described shape.

Examples of the natural spider silk protein include a major dragline silk protein and a flagelliform silk protein.

The major dragline silk protein is produced from spider's major ampullate glands and has a characteristic of excellent toughness. Examples of the major dragline silk protein include major ampullate spidroin MaSp1 or MaSp2 derived from *Nephila clavipes*, ADF3 or ADF4 derived from *Araneus diadematus*, and the like.

The flagelliform silk protein is produced from spider's flagelliform glands, and examples of the flagelliform silk protein include flagelliform silk protein derived from *Nephila clavipes*.

Examples of the polypeptides derived from natural spider silk protein include recombinant spider silk protein, for example, mutants, analogues, derivatives, and the like of natural spider silk protein. The above-described polypeptide is particularly preferably the recombinant spider silk protein of the major dragline silk protein.

The molded article may be a molded article including only natural spider silk protein and/or a polypeptide derived from natural spider silk protein (hereinafter, in some cases, these will be collectively referred to as "spider silk polypeptide") and also may be a molded article in which additive components (for example, a plasticizer, a coloring agent, a filler such as lamellar silicate or basic calcium phosphate, water, synthetic resins, and the like) are added to a spider silk polypeptide. In a case in which additive components of a plasticizer and the like are used, it is preferable to set the amount thereof to 50% by mass or less of the total amount of the spider silk polypeptides. In addition, foreign substances that are generated in a process of obtaining other protein, for example, silk fibroin, soybean protein, casein, keratin, collagen, or milk whey protein or polypeptides may also be included. Meanwhile, the molded article exhibits the effects of the present invention even in a case in which the above-described additive components are not added thereto.

The molded article comprising the spider silk polypeptide preferably has transparency. The transparency can be visually determined, but the molded article preferably has a transmittance of 50% or more in a case in which an optical transmittance measurement instrument is used and, for example, the cumulative time is set to 0.1 seconds in a wavelength range of 220 to 800 nm.

The molded article can be produced using a press molding machine. FIG. 1 is a schematic cross-sectional view of a press molding machine that can be used to produce the molded article. A press molding machine 10 illustrated in FIG. 1 includes a die 2 in which a through hole is formed and which can be heated and an upper side pin 4 and a lower side pin 6 which can be moved up and down in the through hole of the die 2. The molded article can be obtained by introducing the composition including the spider silk polypeptide into a cavity formed by inserting the upper side pin 4 or the lower side pin 6 into the die 2, and pressing the composition with the upper side pin 4 and the lower side pin 6 while heating the die 2.

Figure 2:
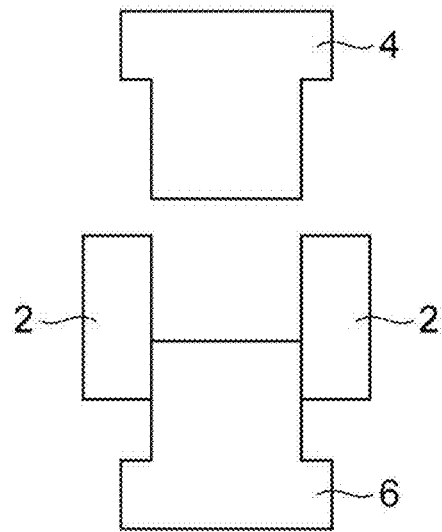
FIG. 2 illustrates schematic cross-sectional views of the press molding machine (a) before the introduction of a composition, (b) immediately after the introduction of the composition, and (c) with the composition in a state of being hot pressed.
Figure 2:
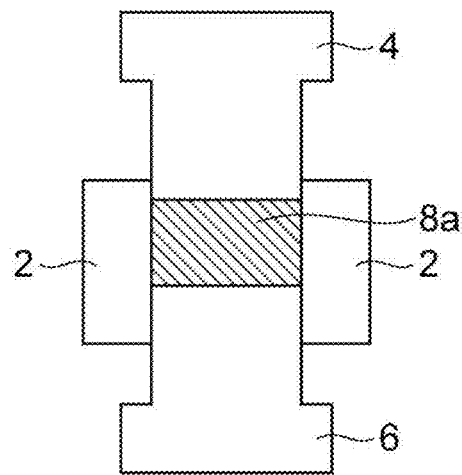
Figure 2:
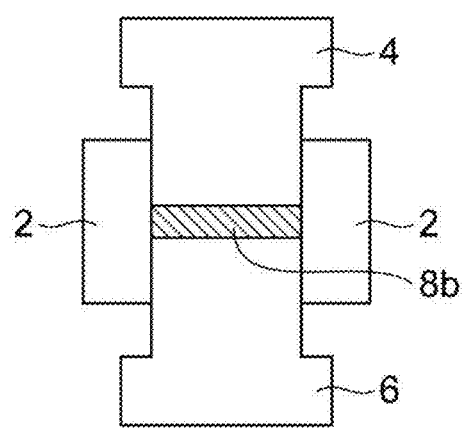

FIG. 2 illustrates step views of obtaining the molded article and are schematic cross-sectional views of the press molding machine (a) before the introduction of the composition, (b) immediately after the introduction of the composition, and (c) with the composition in a state of being heated and pressed. As illustrated in FIG. 2(a), the composition is introduced into the through hole in a state in which only the lower side pin 6 is inserted into the through hole of the die 2, and, as illustrated in FIG. 2(b), the upper side pin 4 is inserted into the through hole of the die 2 and moved down, and the heating of the die 2 is initiated, thereby heating and pressing a composition 8a which is not yet heated and pressed in the through hole. The upper side pin 4 is moved down until a predetermined pressurization force is reached, and heating and pressing are continued until the composition reaches a predetermined temperature in a state illustrated by FIG. 2(c), thereby obtaining a composition 8b which has been hot pressed. After that, the temperature of the die 2 is lowered using a cooler (for example, a spot cooler), the upper side pin 4 or the lower side pin 6 is removed from the die 2 when the composition 8b reaches a predetermined temperature, and the resulting content is taken out, thereby obtaining a molded article. The pressing may be carried out by moving down the upper side pin 4 in a state in which the lower side pin 6 is fixed, but it is also possible to move down the upper side pin 4 and move up the lower side pin 6 at the same time.

The heating is preferably carried out at 80° C. to 300° C., more preferably carried out at 100° C. to 180° C., and still more preferably carried out at 100° C. to 130° C. The pressing is preferably carried out at 5 kN or more, more preferably carried out at 10 kN or more, and still more preferably carried out at 20 kN or more. In addition, the time during which the treatment is continued under predetermined hot pressing conditions after the conditions are satisfied (temperature retention condition) is preferably 0 to 100 minutes, more preferably 1 to 50 minutes, and still more preferably 5 to 30 minutes.

The molded article of the composition comprising a spider silk polypeptide is preferably produced using the polypeptide derived from natural spider silk protein, and thus the production method will be described below in detail.

Examples of the polypeptide derived from the major dragline silk protein which serves as a raw material of the molded article of the composition including a spider silk polypeptide include polypeptides including two or more, preferably including five or more, and more preferably including 10 or more units of an amino-acid sequence represented by Formula 1: REP1-REP2 (1). Alternatively, the polypeptide derived from the major dragline silk protein may be a polypeptide which includes a unit of the amino-acid sequence represented by Formula 1: REP1-REP2 (1) and in which a C terminal sequence is an amino-acid sequence represented by any of SEQ ID Nos. 1 to 3 or an amino-acid sequence having 90% or more homology with the amino-acid sequence represented by any of SEQ ID Nos. 1 to 3. Meanwhile, in the polypeptide derived from the major dragline silk protein, the units of the amino-acid sequence represented by Formula 1: REP1-REP2 (1) may be identical to or different from each other. In a case in which the production of recombinant protein c is carried out using a microbe such as *Escherichia coli* as a host, the molecular weight of the polypeptide derived from the major dragline silk protein is preferably 500 kDa or less, more preferably 300 kDa or less, and still more preferably 200 kDa or less from the viewpoint of productivity.

In Formula 1, REP1 represents polyalanine. In REP1, alanines that are continuously arranged are preferably two or more residues, more preferably three or more residues, still more preferably four or more residues, and particularly preferably five or more residues. In addition, in REP1, alanines that are continuously arranged are preferably 20 or less residues, more preferably 16 or less residues, still more preferably 12 or less residues, and particularly preferably 10 or less residues. In Formula 1, REP2 is an amino-acid sequence made of 10 to 200 residues of amino acid, and the total residue number of glycine, serine, glutamine, and alanine in the amino-acid sequence is 40% or more, preferably 60% or more, and more preferably 70% or more of the total number of amino acid residues.

In the major dragline silk protein, REP1 corresponds to a crystalline region that forms a crystalline β sheet in the fiber, and REP2 corresponds to an amorphous region which is more flexible and lacks a regular structure in a majority area in the fiber. In addition, [REP1-REP2] corresponds to a repetitive region made up of crystalline regions and amorphous regions (repetitive sequence) and is the characteristic sequence of dragline silk protein.

An amino-acid sequence represented by SEQ ID No. 1 is the same as an amino-acid sequence made of 50 residues of amino acid at the C terminal of an amino-acid sequence of ADF3 (NCBI accession number: AAC47010, GI: 1263287), and an amino-acid sequence represented by SEQ ID No. 2 is the same as an amino-acid sequence obtained by removing 20 residues from the C terminal of the amino-acid sequence represented by SEQ ID No. 1, and an amino-acid sequence represented by SEQ ID No. 3 is the same as an amino-acid sequence obtained by removing 29 residues from the C terminal of the amino-acid sequence represented by SEQ ID No. 1.

As the polypeptide including two or more units of the amino-acid sequence represented by Formula 1: REP1-REP2 (1), it is possible to use, for example, a polypeptide made of an amino-acid sequence represented by SEQ ID No. 7. The polypeptide made of the amino-acid sequence represented by SEQ ID No. 7 is an amino-acid sequence of ADF3 (NCBI accession number: AAC47010, GI: 1263287) having an amino-acid sequence (SEQ ID No. 4) made up of an initiation codon, a His10 tag, and a Human rhinovirus 3C protease (HRV3C protease) recognition site added to an N terminal which is mutated so that translation ends at the 543$^{rd}$ amino acid residue.

In addition, as the polypeptide including two or more units of the amino-acid sequence represented by Formula 1: REP1-REP2 (1), it is possible to use a protein which is made of the amino-acid sequence represented by SEQ ID No. 7 in which one or a plurality of amino acids is substituted, deleted, inserted, and/or added, and has a repetitive region made up of crystalline regions and amorphous regions. In the present invention, "one or a plurality" means, for example, 1 to 40, 1 to 35, 1 to 30, 1 to 25, 1 to 20, 1 to 15, 1 to 10, or 1 or several. In addition, in the present invention, "one or several" means 1 to 9, 1 to 8, 1 to 7, 1 to 6, 1 to 5, 1 to 4, 1 to 3, 1 or 2, or 1.

In addition, examples of the polypeptide including two or more units of the amino-acid sequence represented by Formula 1: REP1-REP2 (1) include ADF4-derived recombinant protein having an amino-acid sequence represented by SEQ ID No. 8. The amino-acid sequence represented by SEQ ID No. 8 is an amino-acid sequence obtained by adding the amino-acid sequence (SEQ ID No. 4) made up of an initiation codon, a His10 tag, and a Human rhinovirus 3C protease (HRV3C protease) recognition site to an N terminal of a partial amino-acid sequence of ADF4 (NCBI accession number: AAC47011, GI: 1263289) procured from NCBI database. In addition, as the polypeptide including two or more units of the amino-acid sequence represented by Formula 1: REP1-REP2 (1), a polypeptide which is made of the amino-acid sequence represented by SEQ ID No. 8 in which one or a plurality of amino acids is substituted, deleted, inserted, and/or added, and has a repetitive region made up of crystalline regions and amorphous regions may be used. In addition, examples of the polypeptide including two or more units of the amino-acid sequence represented by Formula 1: REP1-REP2 (1) include MaSp2-derived recombinant protein having an amino-acid sequence represented by SEQ ID No. 9. The amino-acid sequence represented by SEQ ID No. 9 is an amino-acid sequence obtained by adding an amino-acid sequence made up of an initiation codon, a His10 tag, and a Human rhinovirus 3C protease (HRV3C protease) recognition site to an N terminal of a partial amino-acid sequence of MaSp2 (NCBI accession number: AAT75313, GI: 50363147) procured from NCBI database. In addition, as the polypeptide including two or more units of the amino-acid sequence represented by Formula 1: REP1-REP2 (1), a polypeptide which is made of the amino-acid sequence represented by SEQ ID No. 9 in which one or a plurality of amino acids is substituted, deleted, inserted, and/or added, and has a repetitive region made up of crystalline regions and amorphous regions may also be used.

Examples of the polypeptides derived from the flagelliform silk protein include polypeptides including 10 or more, preferably including 20 or more, and more preferably including 30 or more units of an amino-acid sequence represented by Formula 2: REP3 (2). In a case in which the production of recombinant protein is carried out using a microbe such as *Escherichia coli* as a host, the molecular weight of the polypeptide derived from the flagelliform silk protein is preferably 500 kDa or less, more preferably 300 kDa or less, and still more preferably 200 kDa or less from the viewpoint of productivity.

In Formula (2), REP3 refers to an amino-acid sequence constituted of Gly-Pro-Gly-Gly-X (SEQ ID No. 12), and X refers to one amino acid selected from the group consisting of Ala, Ser, Tyr, and Val.

In spider silk, flagelliform silk has a significant characteristic of having a repetitive region which does not have any crystalline regions and is made of an amorphous region. Major dragline silk and the like have a repetitive region made up of crystalline regions and amorphous regions and are thus assumed to have both a high stress and a favorable stretching property. On the other hand, flagelliform silk has a stress that is poorer than that of major dragline silk, but has a favorable stretching property. This is considered to be due to the fact that a majority of flagelliform silk is constituted of an amorphous region.

Examples of the polypeptide including 10 or more units of the amino-acid sequence represented by Formula 2: REP3 (2) include flagelliform silk protein-derived recombinant protein having an amino-acid sequence represented by SEQ ID No. 10. The amino-acid sequence represented by SEQ ID No. 10 is an amino-acid sequence obtained by combining an amino-acid sequence of the 1220$^{th}$ residue through the 1659$^{th}$ residue from an N terminal that corresponds to a repeat portion and a motif of a partial sequence of a flagelliform silk protein of *Nephila clavipes* (NCBI accession number: AAF36090, GI: 7106224) procured from NCBI database (referred to as the PR1 sequence) and a C terminal amino-acid sequence of the 816$^{th}$ residue through the 907$^{th}$ residue from a C terminal of a partial sequence of a flagelliform silk protein of *Nephila clavipes* (NCBI accession number: AAC38847, GI: 2833649) procured from NCBI database and adding the amino-acid sequence (SEQ ID No. 4) made up of an initiation codon, a His10 tag, and an HRV3C protease recognition site to an N terminal of the combined sequence. In addition, as the polypeptide including 10 or more units of the amino-acid sequence represented by Formula 2: REP3 (2), a polypeptide which is made of the amino-acid sequence represented by SEQ ID No. 10 in which one or a plurality of amino acids is substituted, deleted, inserted, and/or added, and has a repetitive region made of an amorphous region may also be used.

The polypeptide can be produced using a host that is transformed by an expression vector containing a gene that codes the polypeptide. A method for producing the gene is not particularly limited, and the gene is produced by amplifying a gene that codes natural spider silk protein from a spider-derived cell by means of a polymerase chain reaction (PCR) or the like and cloning the gene or is chemically synthesized. A method for chemically synthesizing the gene is not particularly limited, and, for example, the gene can be synthesized by linking oligonucleotides that are automatically synthesized with AKTAoligopilot plus 10/100 (manufactured by GE Healthcare Company Japan) or the like by means of PCR on the basis of the amino-acid sequence information of natural spider silk protein procured from the web database of NCBI or the like. At this time, in order to facilitate the refining or confirmation of protein, a gene that codes a protein made of an amino-acid sequence obtained by adding an amino-acid sequence made up of an initiation codon and a His10 tag to an N terminal of the amino-acid sequence may be synthesized.

As the expression vector, it is possible to use a plasmid, a phage, a virus, or the like which is capable of expressing proteins from DNA sequences. The plasmid-type expression vector is not particularly limited as long as the expression vector is capable of expressing the target gene in host cells and is self-amplifiable. For example, in a case in which Escherichia coli Rosetta (DE3) is used as a host, it is possible to use a pET22b(+) plasmid vector, a pCold plasmid vector, or the like. Among these, from the viewpoint of the productivity of protein, the pET22b(+) plasmid vector is preferably used. As the host, it is possible to use, for example, an animal cell, a plant cell, a microbe, or the like.

The polypeptide that is used in the present invention is preferably a polypeptide derived from ADF3 which is one of the two important dragline silk proteins of Araneus diadematus. This polypeptide, basically, has a high strength-elongation degree and a high toughness and also has an advantage of ease of synthesis.

EXAMPLES

Hereinafter, the present invention will be described in more detail using examples, but the present invention is not limited to these examples within the scope of the technical concept of the present invention.

<Gene Synthesis>

(1) Synthesis of Gene of ADF3Kai

A partial amino-acid sequence of ADF3 which is one of the two important dragline silk proteins of Araneus diadematus (NCBI accession number: AAC47010, GI: 1263287) was acquired from the web database of NCBI, and the synthesis of a gene that codes an amino-acid sequence (SEQ ID No. 5) obtained by adding (SEQ ID No. 4) made up of an initiation codon, a His10 tag, and a Human rhinovirus 3C protease (HRV3C protease) recognition site to an N terminal of the same sequence was entrusted to GenScript Japan Inc. As a result, a pUC57 vector (having an NdeI site at right upstream region of a 5' terminal of the gene and an Xba I site at right downstream region of the 5' terminal) into which a gene of ADF3Kai made of a base sequence represented by SEQ ID No. 6 was introduced was acquired. Then, a restriction enzyme treatment was carried out on the same gene using Nde I and EcoR I, and the gene was recombined to a pET22b(+) expression vector.

(2) Synthesis of Gene of ADF3Kai-noNR

The above-obtained pET22b(+) expression vector into which the gene of ADF3Kai was used as a template, and a codon GTG corresponding to the $543^{rd}$ amino acid residue valine (Val) in the amino-acid sequence (SEQ ID No. 5) of ADF3Kai was mutated to a termination codon TAA by means of site-directed mutagenesis using PrimeStar MutagenesisBasal Kit (manufactured by Takara Bio Inc.), thereby constructing a gene of ADF3Kai-noNR represented by SEQ ID No. 11 on pET22b(+). The accuracy of the mutagenesis was confirmed from a sequence reaction for which 3130×1 Genetic Analyzer (Applied Biosystems) was used. Meanwhile, the amino-acid sequence of ADF3Kai-noNR is as indicated by SEQ ID No. 7.

<Expression of Protein>

The pET22b(+) expression vector including a gene sequence of the above-obtained ADF3Kai-noNR was transformed to Escherichia coli Rosetta (DE3). The obtained single colony was cultured for 15 hours in a 2 mL LB culture medium including ampicillin, 1.4 mL of the resulting culture liquid was added to a 140 mL LB culture medium including ampicillin, and the culture liquid was cultured under conditions of 37° C. and 200 rpm until $OD_{600}$ of the culture liquid reached 3.5. Next, the culture liquid having $OD_{600}$ of 3.5 was added to a 7 L 2xYT culture medium including ampicillin together with 140 mL of 50% glucose and was further cultured until $OD_{600}$ reached 4.0. Then, isopropyl-β-thiogalactopyranoside (IPTG) was added to the obtained culture liquid having $OD_{600}$ of 4.0 so that the final concentration reached 0.5 mM, thereby inducing protein expression. After two hours elapsed from the addition of IPTG, the culture liquid was centrifugally separated, and a bacterial body was collected. As a result of electrophoresing protein solutions prepared from the culture liquid before that addition of IPTG and after the addition of IPTG in polyacrylamide gels, bands having a target size were observed depending on the addition of IPTG, and it was confirmed that target protein was expressed. Escherichia coli that expressed the protein of ADF3Kai-noNR was stored in a freezer (−20° C.).

<Polypeptide Preparation Example>

(I) Approximately 4.5 g of the bacterial body of Escherichia coli that expressed the protein of ADF3Kai-noNR and 30 ml of a buffer solution AI (20 mM of Tris-HCl, pH 7.4) were added to a centrifuge tube (50 mL), the bacterial body was dispersed using a mixer (manufactured by General Electric, SI-0286, level 10), then, centrifugal separation (10,000 rpm, 10 minutes, room temperature) was carried out using a centrifugal separator (manufactured by Tomy Seiko Co., Ltd., MX-305), and the supernatant was removed.

(II) 30 mL of a buffer solution AI and 0.3 mL of 0.1 M PMSF (dissolved using isopropanol) were added to the precipitate (bacterial body) obtained by the centrifugal separation and were dispersed for three minutes using the mixer (level 10) manufactured by General Electric. After that, the bacterial body was crushed using an ultrasonic crusher (manufactured by Sonic & Materials, Inc., VCX500), and centrifugal separation (10,000 rpm, 10 minutes, room temperature) was carried out.

(III) 30 mL of the buffer solution AI was added to the precipitate obtained by the centrifugal separation, was dispersed for three minutes using a mixer (manufactured by IKA, T18 basic ULTRA-TURRAX, level 2) manufactured by General Electric, then, centrifugal separation (10,000 rpm, 10 minutes, room temperature) was carried out using the centrifugal separator manufactured by Tomy Seiko Co., Ltd., and the supernatant was removed.

(IV) A 7.5 M urea buffer solution I (7.5 M of urea, 10 mM of sodium dihydrogen phosphate, 20 mM of NaCl, 1 mM of Tris-HCl, pH 7.0) was added to the centrifuge tube from which the supernatant was removed, and the precipitation was favorably dispersed using the ultrasonic crusher manufactured by SMT (level 7). After that, the precipitate was dissolved for 120 minutes using a shaker manufactured by Taitec Corporation (200 rpm, 60° C.). A protein solution after the dissolution was centrifugally separated (11,000×g, 10 minutes, room temperature) using the centrifugal separator manufactured by Tomy Seiko Co., Ltd., and the supernatant was dialyzed using a dialysis tube (manufactured by Sanko Junyaku Co., Ltd., cellulose tube 36/32). White agglomerated protein obtained after the dialysis was collected by means of centrifugal separation, water was removed using a freeze dryer, and freeze-dried powder was collected. The degree of refining of the target protein ADF3Kai-noNR in the obtained freeze-dried powder was confirmed by image-analyzing the results of the polyacrylamide gel electrophoresis (CBB dyeing) of the powder using Totallab (Nonlinear Dynamics Ltd.). As a result, the degree of refining of ADF3Kai-noNR was approximately 85%.

Example 1

<Method for Producing Molded Article>

1.35 g of the freeze-dried powder obtained in the "polypeptide preparation example" (hereinafter, referred to as "sample") was weighed, and this sample was introduced into the through hole of the die 2 (a cylindrical die having a rectangular through hole having a 35 mm×15 mm cross section) of the press molding machine 10 illustrated in FIG. 1. At this time, the sample was added so that it became uniform thickness. After the entire sample was introduced, the heating of the die 2 was initiated, and the upper side pin 4 and the lower side pin 6 were inserted into the through hole using a hand presser (manufactured by NPa System Co., Ltd., NT-100H-V09), thereby pressing the sample. At this time, the pressurization condition of the sample was controlled to be 40 kN. The heating was stopped when the temperature of the sample reached 200° C., the sample was cooled using a spot cooler (manufactured by Trusco Nakayama Corporation, TS-25EP-1) and was removed when the temperature of the sample reached 50° C., and deburring was carried out, thereby obtaining a 35 mm×15 mm×2 mm rectangular molded article.

In Example 1, the heating was stopped when the temperature of the sample reached 200° C., the sample was cooled using the spot cooler and was removed when the temperature of the sample reached 50° C. That is, the heating temperature (X) was 200° C., and the annealing time (Y) was 0 minutes since the rapid cooling was initiated immediately after the heating temperature was reached.

Example 2

A molded article was obtained in the same manner as in Example 1 except for the fact that the heating temperature (X) was set to 100° C., the annealing time (Y) was set to 30 minutes, and the pressurization condition was set to 30 kN.

<Methods for Measuring Bending Elastic Modulus and Bending Strength>

After the obtained molded article was left to stand for one day in a constant temperature and humidity tank (manufactured by ESPEC Corp., LHL-113) under conditions of 20° C./65%, the following measurements were carried out.

That is, a three-point bending test was carried out using a basket jig in an autograph (manufactured by Shimadzu Corporation, AG-Xplus). A load cell used was 50 kN. At this time, the distance between the support points for three-point bending was fixed to 27 mm, and the measurement rate was set to 1 mm/minute. In addition, the size of the molded article was measured using a microcaliper, and the molded article was installed in the jig and was measured. The bending elastic modulus was obtained from a displacement (strain) of up to 0.05 to 0.25%.

<Method for Measuring Transparency>

For the obtained molded articles, the transparency in the thickness direction (2 mm-thick) was visually measured, and molded articles that were transparent were evaluated as O, and molded articles that were not transparent were evaluated as X. That is, the transparency was confirmed from whether or not the logo was visible when the molded article was placed on paper on which the logo of Spiber Inc. was printed.

Comparative Examples 1 to 4

35 mm×15 mm×2 mm rectangular formed articles were obtained in the same manner as in Example 1 using polyether ether ketone (PEEK), polycarbonate (PC), poly (methyl methacrylate) (PMMA), and an ABS resin (ABS). These formed articles were left to stand for one day in the constant temperature and humidity tank (manufactured by ESPEC Corp., LHL-113) under conditions of 20° C./65%, and then the bending elastic moduli, the bending strengths, and the transparency were measured in the same manner as in Example 1.

Figure 3:
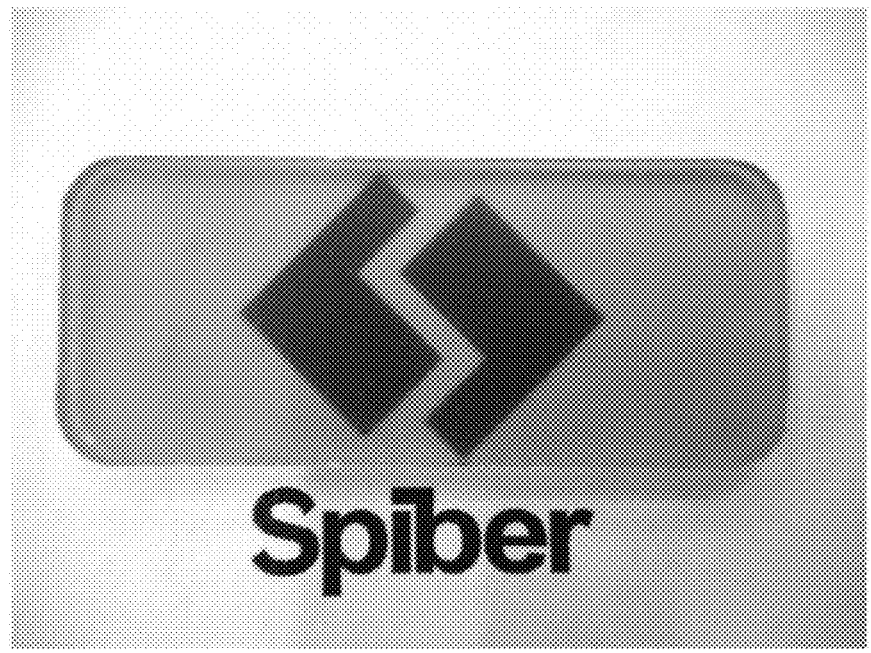
FIG. 3 is a photograph of a molded article of Example 1.

The results of the example and the comparative examples are summarized in Table 1. A photograph of the molded article used to evaluate the transparency of Example 1 is illustrated in FIG. 3.

TABLE 1

|  | Bending Elastic Modulus (GPa) | Bending Strength (MPa) | Transparency |
|---|---|---|---|
| Example 1 | 5.39 | 74 | O |
| Example 2 | 6.6 | 64.6 | O |
| Comparative Example 1 (PEEK) | 4.4 | 171 | X |
| Comparative Example 2 (PC) | 2.68 | 97.3 | O |
| Comparative Example 3 (PMMA) | 3.2 | 105 | O |
| Comparative Example 4 (ABS) | 2.32 | 62.9 | X |

Examples 2 to 17

Molded articles were obtained in the same manner as in Example 1 except for the fact that the heating temperature (X) and the annealing time (Y) were changed as shown in Table 2 and the pressurization condition was set to 30 kN.

TABLE 2

|  | Heating Temperature X (° C.) | Annealing Time Y (Minutes) |
|---|---|---|
| Example 2 | 110 | 0 |
| Example 3 | 120 | 0 |
| Example 4 | 130 | 0 |
| Example 5 | 140 | 0 |

TABLE 2-continued

|  | Heating Temperature X (° C.) | Annealing Time Y (Minutes) |
|---|---|---|
| Example 6 | 160 | 0 |
| Example 7 | 180 | 0 |
| Example 8 | 90 | 5 |
| Example 9 | 100 | 5 |
| Example 10 | 110 | 5 |
| Example 11 | 120 | 5 |
| Example 12 | 90 | 15 |
| Example 13 | 120 | 15 |
| Example 14 | 80 | 30 |
| Example 15 | 90 | 30 |
| Example 16 | 110 | 30 |
| Example 17 | 120 | 30 |

Examples 18 to 23

Molded articles were obtained in the same manner as in Example 1 except for the fact that the heating temperature (X), the annealing time (Y), and the pressing condition were set as shown in Table 3.

TABLE 3

|  | Heating Temperature X (° C.) | Annealing Time Y (Minutes) | Pressing Condition (kN) |
|---|---|---|---|
| Example 18 | 90 | 0 | 40 |
| Example 19 | 100 | 0 | 40 |
| Example 20 | 110 | 0 | 40 |
| Example 21 | 120 | 0 | 40 |
| Example 22 | 90 | 0 | 50 |
| Example 23 | 100 | 0 | 50 |

For Examples 5 to 7, 16 and 17, the bending elastic moduli and the bending strengths were measured and are summarized in Table 4.

TABLE 4

|  | Heating Temperature X (° C.) | Annealing Time Y (Minutes) | Bending Elastic Modulus (GPa) | Bending Strength (MPa) |
|---|---|---|---|---|
| Example 5 | 140 | 0 | 5.2 | 52.1 |
| Example 6 | 160 | 0 | 5.8 | 56.7 |
| Example 7 | 180 | 0 | 5.7 | 63.5 |
| Example 16 | 110 | 30 | 6.3 | 67.1 |
| Example 17 | 120 | 30 | 5.9 | 62.5 |

REFERENCE SIGNS LIST

2: DIE, 4: UPPER SIDE PIN, 6: LOWER SIDE PIN, 8a: COMPOSITION BEFORE HOT PRESSING, 8b: COMPOSITION AFTER HOT PRESSING, 10: PRESS MOLDING MACHINE

Sequence Listing

The invention claimed is:

1. A non-fibrous, hot-press molded, fused article of a composition comprising a refined recombinant polypeptide, wherein the polypeptide is at least one kind selected from the group consisting of natural spider silk protein and polypeptides derived from natural spider silk protein, wherein the natural spider silk protein and polypeptides derived from natural spider silk protein comprise a unit of the amino acid sequence represented by Formula 1:

REP1-REP2            (1), wherein 2 to 20 alanine amino acid residues are continuously arranged in REP1, and REP2 is an amino acid sequence of 10 to 200 amino acid residues, in which the total amino acid residue number of glycine, serine, glutamine, and alanine in the amino acid sequence is 40% or more of the total number of the amino acid residues, and wherein the non-fibrous, hot-press molded, fused article has a bending elastic modulus of more than 4.5 GPa.

2. The non-fibrous, hot press molded, fused article according to claim 1, wherein the bending elastic modulus is 4.7 GPa or more and 15.0 GPa or less.

3. The non-fibrous, hot press molded, fused article according to claim 2, wherein the bending elastic modulus is more than 5.0 GPa or more and 10.0 GPa or less.

4. The non-fibrous, hot press molded, fused article according to claim 3, wherein the bending elastic modulus is more than 5.2 GPa or more and 7.0 GPa or less.

5. The non-fibrous, hot press molded, fused article according to claim 1, wherein the non-fibrous, hot press molded, fused article has a transmittance of 50% or more in a case in which an optical transmittance measurement instrument is used and a cumulative time is set to 0.1 seconds in a wavelength range of 220 to 800 nm.

6. The non-fibrous, hot press molded, fused article according to claim 5, wherein the bending elastic modulus of more than 4.7 GPa or more and 15.0 GPa or less.

7. The non-fibrous, hot press molded, fused article according to claim 6, wherein the bending elastic modulus is more than 5.0 GPa or more and 10.0 GPa or less.

8. The non-fibrous, hot press molded, fused article according to claim 7, wherein the bending elastic modulus is more than 5.2 GPa or more and 7.0 GPa or less.

* * * * *